US006982343B2

(12) United States Patent
Chaturvedi et al.

(10) Patent No.: US 6,982,343 B2
(45) Date of Patent: Jan. 3, 2006

(54) TREATMENT OF MIXED METAL OXIDE CATALYST

(75) Inventors: Sanjay Chaturvedi, Horsham, PA (US); Anne Mae Gaffney, West Chester, PA (US); Dominique Hung Nhu Le, Upper Darby, PA (US)

(73) Assignee: Rohm and Haas Company, Philadelphia, PA (US)

( * ) Notice: Subject to any disclaimer, the term of this patent is extended or adjusted under 35 U.S.C. 154(b) by 350 days.

(21) Appl. No.: 10/272,893

(22) Filed: Oct. 17, 2002

(65) Prior Publication Data

US 2003/0135064 A1    Jul. 17, 2003

Related U.S. Application Data

(60) Provisional application No. 60/339,408, filed on Oct. 26, 2001.

(51) Int. Cl.
  *C07C 253/00*    (2006.01)
  *C07C 51/16*    (2006.01)
  *B01J 23/00*    (2006.01)

(52) U.S. Cl. .................... 558/323; 562/547; 562/549; 502/311; 502/312

(58) Field of Classification Search ............ 502/311, 502/312, 302–304, 321–322, 255, 248, 206, 502/211, 110, 113, 117; 558/323; 562/534, 562/535, 547, 549
See application file for complete search history.

(56) References Cited

U.S. PATENT DOCUMENTS

| | | | |
|---|---|---|---|
| 3,956,376 A | | 5/1976 | Ferlazzo et al. |
| 5,281,745 A | | 1/1994 | Ushikubo et al. ........... 558/319 |
| 5,380,933 A | | 1/1995 | Ushikubo et al. ........... 562/549 |
| 5,472,925 A | | 12/1995 | Ushikubo et al. |
| 5,973,186 A | | 10/1999 | Midorikawa et al. |
| 6,037,304 A | * | 3/2000 | Abdulwahed et al. ....... 502/300 |
| 6,043,185 A | | 3/2000 | Cirjak et al. ................. 502/311 |
| 6,043,186 A | * | 3/2000 | Komada et al. ............. 502/312 |
| 6,060,422 A | | 5/2000 | Takahashi et al. |
| 6,063,728 A | * | 5/2000 | Hinago et al. ............... 502/300 |
| 6,114,278 A | * | 9/2000 | Karim et al. ................ 502/312 |
| 6,124,233 A | * | 9/2000 | Abdulwahed et al. ....... 502/312 |
| 6,143,690 A | * | 11/2000 | Komada et al. ............. 502/211 |
| 6,383,978 B1 | * | 5/2002 | Bogan, Jr. .................... 502/311 |
| 6,403,525 B1 | * | 6/2002 | Chaturvedi et al. ......... 502/311 |
| 6,407,280 B1 | * | 6/2002 | Chaturvedi et al. ......... 558/319 |
| 6,432,870 B1 | * | 8/2002 | Tu et al. ...................... 502/305 |
| 6,504,053 B1 | * | 1/2003 | Chaturvedi et al. ......... 562/549 |
| 6,514,902 B1 | * | 2/2003 | Inoue et al. ................. 502/305 |
| 6,559,085 B1 | * | 5/2003 | Sasaki et al. ................. 502/22 |
| 6,589,907 B2 | * | 7/2003 | Chaturvedi et al. ......... 502/311 |
| 6,610,629 B2 | * | 8/2003 | Hinago et al. ............... 502/300 |
| 6,624,111 B2 | * | 9/2003 | Chaturvedi et al. ......... 502/312 |
| 6,638,891 B2 | * | 10/2003 | Karim et al. ................ 502/302 |
| 6,642,173 B2 | * | 11/2003 | Bogan, Jr. .................... 502/311 |
| 6,642,174 B2 | * | 11/2003 | Gaffney et al. .............. 502/311 |
| 6,645,906 B2 | * | 11/2003 | Bogan et al. ................ 502/311 |
| 6,656,873 B2 | * | 12/2003 | Chaturvedi et al. ......... 502/312 |
| 6,747,168 B2 | * | 6/2004 | Chaturvedi et al. ......... 558/319 |
| 6,777,571 B2 | * | 8/2004 | Chaturvedi et al. ......... 558/323 |

FOREIGN PATENT DOCUMENTS

| | | |
|---|---|---|
| DE | 196 30 832 | 2/1998 |
| EP | 0 608 838 | 8/1994 |
| EP | 0 630 879 B1 | 1/1998 |
| EP | 0 962 253 | 12/1999 |
| EP | 1 249 274 A | 10/2002 |
| EP | 1 254 707 A | 11/2002 |
| JP | 6-228073 | 8/1994 |
| JP | 07-53448 | 2/1995 |
| JP | 2000-37623 | 2/2000 |
| WO | WO 00/09260 | 2/2000 |
| WO | WO 00/29106 | 5/2000 |

OTHER PUBLICATIONS

Patent Abstracts of Japan—JP Publ. No. 08057319 (Mar. 5, 1996), JP Appln. No. 06199561.

* cited by examiner

*Primary Examiner*—Cam N. Nguyen
(74) *Attorney, Agent, or Firm*—Marcella M. Bodner; Alan Holler

(57) ABSTRACT

A catalyst comprising a mixed metal oxide is useful for the vapor phase oxidation of an alkane or a mixture of an alkane and an alkene to an unsaturated carboxylic acid and for the vapor phase ammoxidation of an alkane or a mixture of an alkane and an alkene to an unsaturated nitrile. The catalyst is treated with a source of hydrogen, an alcohol, a source of $NO_x$ or a mixture thereof.

5 Claims, No Drawings

TREATMENT OF MIXED METAL OXIDE CATALYST

CROSS REFERENCE TO RELATED PATENT APPLICATION

This is a non-provisional application of prior U.S. provisional application Ser. No. 60/339,408 filed on Oct. 26, 2001, now abandoned.

The present invention relates to an improved catalyst for the oxidation of alkanes or a mixture of alkanes and alkenes to their corresponding unsaturated carboxylic acids by vapor phase catalytic oxidation; to a method of making the catalyst; and to a process for the vapor phase catalytic oxidation of alkanes or a mixture of alkanes and alkenes to their corresponding unsaturated carboxylic acids. The present invention also relates to a method of producing unsaturated nitriles by subjecting alkanes or a mixture of alkanes and alkenes to vapor phase catalytic oxidation in the presence of ammonia.

Nitriles, such as acrylonitrile and methacrylonitrile, have been industrially produced as important intermediates for the preparation of fibers, synthetic resins, synthetic rubbers, and the like. The most popular method for producing such nitrites is to subject an olefin such as propene or isobutene to a catalytic reaction with ammonia and oxygen in the presence of a catalyst in a gaseous phase at a high temperature. Known catalysts for conducting this reaction include a Mo—Bi—P—O catalyst, a V—Sb—O catalyst, an Sb—U—V—Ni—O catalyst, a Sb—Sn—O catalyst, a V—Sb—W—P—O catalyst and a catalyst obtained by mechanically mixing a V—Sb—W—O oxide and a Bi—Ce—Mo—W—O oxide. However, in view of the price difference between propane and propene or between isobutane and isobutene, attention has been drawn to the development of a method for producing acrylonitrile or methacrylonitrile by an ammoxidation reaction wherein a lower alkane, such as propane or isobutane, is used as a starting material, and it is catalytically reacted with ammonia and oxygen in a gaseous phase in the presence of a catalyst.

In particular, U.S. Pat. No. 5,281,745 discloses a method for producing an unsaturated nitrile comprising subjecting an alkane and ammonia in the gaseous state to catalytic oxidation in the presence of a catalyst which satisfies the conditions:

(1) the mixed metal oxide catalyst is represented by the empirical formula $Mo_aV_bTe_cX_xO_n$ wherein X is at least one element selected from the group consisting of niobium, tantalum, tungsten, titanium, aluminum, zirconium, chromium, manganese, iron, ruthenium, cobalt, rhodium, nickel, palladium, platinum, antimony, bismuth, boron and cerium and, when a=1, b=0.01 to 1.0, c=0.01 to 1.0, x=0.01 to 1.0 and n is a number such that the total valency of the metal elements is satisfied; and (2) the catalyst has X-ray diffraction peaks at the following angles (±0.3°) of 2θ in its X-ray diffraction pattern: 22.1°, 28.2°, 36.2°, 45.2° and 50.0°.

Similarly, Japanese Laid-Open Patent Application Publication No. 6-228073 discloses a method of nitrile preparation comprising reacting an alkane in a gas phase contact reaction with ammonia in the presence of a mixed metal oxide catalyst of the formula $W_aV_bTe_cX_xO_n$ wherein X represents one or more elements selected from niobium, tantalum, titanium, aluminum, zirconium, chromium, manganese, iron, ruthenium, cobalt, rhodium, nickel, palladium, platinum, antimony, bismuth, indium and cerium and, when a=1, b=0.01 to 1.0, c=0.01 to 1.0, x=0.01 to 1.0 and n is determined by the oxide form of the elements.

U.S. Pat. No. 6,043,185 also discloses a catalyst useful in the manufacture of acrylonitrile or methacrylonitrile by the catalytic reaction in the vapor phase of a paraffin selected from propane and isobutane with molecular oxygen and ammonia by catalytic contact of the reactants in a reaction zone with a catalyst, wherein the catalyst has the empirical formula $Mo_aV_bSb_cGa_dX_eO_x$ where X is one or more of As, Te, Se, Nb, Ta, W, Ti, Zr, Cr, Mn, Fe, Ru, Co, Rh, Ni, Pd, Pt, B, In, Ce, Re, Ir, Ge, Sn, Bi, Y, Pr, an alkali metal and an alkaline earth metal; and when a=1, b=0.0 to 0.99, c=0.01 to 0.9, d=0.01 to 0.5, e=0.0 to 1.0 and x is determined by the oxidation state of the cations present.

Unsaturated carboxylic acids such as acrylic acid and methacrylic acid are industrially important as starting materials for various synthetic resins, coating materials and plasticizers. Commercially, the current process for acrylic acid manufacture involves a two-step catalytic oxidation reaction starting with a propene feed. In the first stage, propene is converted to acrolein over a modified bismuth molybdate catalyst. In the second stage, acrolein product from the first stage is converted to acrylic acid using a catalyst composed of mainly molybdenum and vanadium oxides. In most cases, the catalyst formulations are proprietary to the catalyst supplier, but the technology is well established. Moreover, there is an incentive to develop a single step process to prepare the unsaturated acid from its corresponding alkene. Therefore, the prior art describes cases where complex metal oxide catalysts are utilized for the preparation of unsaturated acid from a corresponding alkene in a single step.

European Published Patent Application No. 0 630 879 B1 discloses a process for producing an unsaturated aldehyde and a carboxylic acid which comprises subjecting propene, isobutene or tertiary butanol to gas phase catalytic oxidation with molecular oxygen in the presence of (i) a catalyst composite oxide represented by the formula $Mo_aBi_bFe_cA_dB_eC_fD_gO_x$ wherein A represents Ni and/or Co, B represents at least one element selected from Mn, Zn, Ca, Mg, Sn and Pb, C represents at least one element selected from P, B, As, Te, W, Sb and Si, and D represents at least one element selected from K, Rb, Cs and Tl; and wherein, when a=12, 0<b≦10, 0<c≦10, 1≦d≦10, 0≦e≦10, 0≦f≦20 and 0≦g≦2, and x has a value dependent on the oxidation state of the other elements; and (ii) a molybdenum oxide which in itself is substantially inert to said gas phase catalytic oxidation to provide the corresponding unsaturated aldehyde and unsaturated carboxylic acid.

Japanese Laid-Open Patent Application Publication No. 07-053448 discloses the manufacture of acrylic acid by the gas-phase catalytic oxidation of propene in the presence of mixed metal oxides containing Mo, V, Te, O and X wherein X is at least one of Nb, Ta, W, Ti, Al, Zr, Cr, Mn, Fe, Ru, Co, Rh, Ni, Pd, Pt, Sb, Bi, B, In, Li, Na, K, Rb, Cs and Ce.

Published International Application No. WO 00/09260 discloses a catalyst for selective oxidation of propene to acrylic acid and acrolein containing a catalyst composition comprising the elements Mo, V, La, Pd, Nb and X in the following ratio:

wherein X is Cu or Cr or a mixture thereof,
a is 1,
b is 0.01 to 0.9,
c is >0 to 0.2
d is 0.0000001 to 0.2,
e is 0 to 0.2, and
f is 0 to 0.2; and wherein the numerical values of a, b, c, d, e and f represent the relative gram-atom ratios of the elements Mo, V, La, Pd, Nb and X, respectively, in the catalyst and the elements are present in combination with oxygen.

Commercial incentives also exist for producing acrylic acid using a lower cost propane feed. Therefore, the prior art describes cases wherein a mixed metal oxide catalyst is used to convert propane to acrylic acid in one step.

U.S. Pat. No. 5,380,933 discloses a method for producing an unsaturated carboxylic acid comprising subjecting an alkane to a vapor phase catalytic oxidation reaction in the presence of a catalyst containing a mixed metal oxide comprising, as essential components, Mo, V, Te, O and X, wherein X is at least one element selected from the group consisting of niobium, tantalum, tungsten, titanium, aluminum, zirconium, chromium, manganese, iron, ruthenium, cobalt, rhodium, nickel, palladium, platinum, antimony, bismuth, boron, indium and cerium; and wherein the proportions of the respective essential components, based on the total amount of the essential components, exclusive of oxygen, satisfy the following relationships:

$$0.25 < r(Mo) < 0.98,\ 0.003 < r(V) < 0.5,\ 0.003 < r(Te) < 0.5$$
$$\text{and } 0.003 < r(X) < 0.5,$$

wherein r(Mo), r(V), r(Te) and r(X) are the molar fractions of Mo, V, Te and X, respectively, based on the total amount of the essential components exclusive of oxygen.

Published International Application No. WO 00/29106 discloses a catalyst for selective oxidation of propane to oxygenated products including acrylic acid, acrolein and acetic acid, said catalyst system containing a catalyst composition comprising

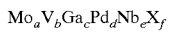

wherein X is at least one element selected from La, Te, Ge, Zn, Si, In and W,
a is 1,
b is 0.01 to 0.9,
c is >0 to 0.2,
d is 0.0000001 to 0.2,
e is >0 to 0.2, and
f is 0.0 to 0.5; and wherein the numerical values of a, b, c, d, e and f represent the relative gram-atom ratios of the elements Mo, V, Ga, Pd, Nb and X, respectively, in the catalyst and the elements are present in combination with oxygen.

Japanese Laid-Open Patent Application Publication No. 2000-037623 discloses a method for producing an unsaturated carboxylic acid comprising subjecting an alkane to a vapor phase catalytic oxidation in the presence of a catalyst having the empirical formula

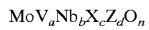

wherein X is at least one element selected from the group consisting of Te and Sb, Z is at least one element selected from the group consisting of W, Cr, Ta, Ti, Zr, Hf, Mn, Re, Fe, Ru, Co, Rh, Ni, Pd, Pt, Ag, Zn, B, Al, Ga, In, Ge, Sn, Pb, P, Bi, Y, rare earth elements and alkaline earth elements, $0.1 \leq a \leq 1.0$, $0.01 \leq b \leq 1.0$, $0.01 \leq c \leq 1.0$, $0 \leq d \leq 1.0$ and n is determined by the oxidation states of the other elements.

Despite the above-noted attempts to provide new and improved catalysts for the oxidation of alkanes to unsaturated carboxylic acids and for the ammoxidation of alkanes to unsaturated nitriles, one impediment to the provision of a commercially viable process for such catalytic oxidations is the identification of a catalyst providing adequate conversion and suitable selectivity, thereby providing sufficient yield of the unsaturated product. Another limitation to the prior art is lack of providing a commercially viable, three dimensional structure onto which one may support the catalyst or into which one may formulate the catalyst.

By the present invention, there are provided catalysts wherein the performance is enhanced by treatment of the catalyst with a gaseous treatment agent, and more particularly a treatment agent selected from the group consisting of hydrogen, alkanols, a source of $NO_x$ (particularly a gaseous source) and mixtures thereof.

Thus, in a first aspect, the present invention provides a catalyst comprising a mixed metal oxide having the empirical formula $A_aD_bE_cX_dO_e$, wherein A is at least one element selected from the group consisting of Mo and W, D is at least one element selected from the group consisting of V and Ce, E is at least one element selected from the group consisting of Te, Sb and Se, and X is at least one element selected from the group consisting of Nb, Ta, Ti, Al, Zr, Cr, Mn, Fe, Ru, Co, Rh, Ni, Pt, Sb, Bi, B, In, As, Ge, Sn, Li, Na, K, Rb, Cs, Fr, Be, Mg, Ca, Sr, Ba, Ra, Hf, Ag, Pb, P, Pm, Eu, Gd, Dy, Ho, Er, Tm, Yb and Lu; and a=1, b=0.01 to 1.0, c=0.01 to 1.0, d=0.01 to 1.0, and e is dependent on the oxidation state of said other elements. The catalyst composition, during or after calcination, is treated with a treatment agent selected from the group consisting of hydrogen, alcohols, a source of $NO_x$ and mixtures thereof.

As will be seen from the discussion herein, preferably the treatment agent is contacted with the catalyst (which may include precursors thereof) while the treatment agent is in a liquid or gaseous state. Thus, any of a number of suitable delivery techniques may be employed to bring the treatment agent into contact with the catalyst, including those such as gas flow, vapor reflux, saturation, or the like. Thus, the process may be performed continuously, in batch or a combination thereof.

Accordingly, preferred treatment agents may be selected from one or more of hydrogen, alkanols (such as methanol, ethanol, propanol or higher order alcohols), diols, or a source of $NO_x$ (preferably a gaseous source) selected from the group consisting of $NO$, $N_2O$, $NO_2$ and mixtures thereof. The treatment agents may be provided in pure form, or they may diluted or otherwise admixed with other fluid carriers.

Though other crystallographic results are possible, one preferred resulting catalyst exhibits the following five main diffraction peaks at specific diffraction angles 2θ in the X-ray diffraction pattern of the promoted mixed metal oxide (as measured using Cu-Kα radiation as the source):

| X-ray lattice plane | | |
|---|---|---|
| Diffraction angle 2θ (±0.3°) | Spacing medium (Å) | Relative intensity |
| 22.1° | 4.02 | 100 |
| 28.2° | 3.16 | 20~150 |
| 36.2° | 2.48 | 5~60 |
| 45.2° | 2.00 | 2~40 |
| 50.0° | 1.82 | 2~40 |

The intensity of the X-ray diffraction peaks may vary upon the measuring of each crystal. However, the intensity, relative to the peak intensity at 22.1° being 100, is usually within the above ranges. Generally, the peak intensities at 2θ=22.1° and 28.2° are distinctly observed.

The present mixed metal oxide can be prepared in a suitable manner such as that illustrated in the following discussion. Thus, in a first step a slurry or solution may be formed by admixing metal compounds, preferably at least one of which contains oxygen, and at least one solvent in appropriate amounts to form the slurry or solution. Preferably, a solution is formed at this stage of the catalyst preparation. Generally, the metal compounds contain elements A, D, E, X and O, as previously defined.

Suitable solvents include water; alcohols including, but not limited to, methanol, ethanol, propanol, and diols, etc.; as well as other polar solvents known in the art. Generally, water is preferred. The water is any water suitable for use in chemical syntheses including, without limitation, distilled water and de-ionized water. The amount of water present is preferably an amount sufficient to keep the elements substantially in solution long enough to avoid or minimize compositional and/or phase segregation during the preparation steps. Accordingly, the amount of water will vary according to the amounts and solubilities of the materials combined. However, as stated above, the amount of water is preferably sufficient to ensure an aqueous solution is formed, and not a slurry, at the time of mixing.

For example, when a mixed metal oxide of the formula $Mo_aV_bTe_cNb_dO_e$ wherein the element A is Mo, the element M is V, the element N is Te and the element X is Nb, is to be prepared, an aqueous solution of niobium oxalate may be added to an aqueous solution or slurry of ammonium heptamolybdate, ammonium metavanadate and telluric acid, so that the atomic ratio of the respective metal elements would be in the prescribed proportions.

Once the aqueous slurry or solution (preferably a solution) is formed, the water is removed by any suitable method, known in the art, to form a catalyst precursor. Such methods include, without limitation, vacuum drying, freeze drying, spray drying, rotary evaporation and air drying. Vacuum drying is generally performed at pressures ranging from 10 mmHg to 500 mmHg. Freeze drying typically entails freezing the slurry or solution, using, for instance, liquid nitrogen, and drying the frozen slurry or solution under vacuum. Spray drying is generally performed under an inert atmosphere such as nitrogen or argon, with an inlet temperature ranging from 125° C. to 200° C. and an outlet temperature ranging from 75° C. to 150° C. Rotary evaporation is generally performed at a bath temperature of from 25° C. to 90° C. and at a pressure of from 10 mmHg to 760 mmHg, preferably at a bath temperature of from 40° to 90° C. and at a pressure of from 10 mmHg to 350 mmHg, more preferably at a bath temperature of from 40° C. to 60° C. and at a pressure of from 10 mmHg to 40 mmHg. Air drying may be effected at temperatures ranging from 25° C. to 90° C. Rotary evaporation or air drying are generally preferred.

Once obtained, the catalyst precursor is calcined. The calcination may be conducted in an oxygen-containing atmosphere or in the substantial absence of oxygen, e.g., in an inert atmosphere or in vacuo. The inert atmosphere may be any material which is substantially inert, i.e., does not react or interact with, the catalyst precursor. Suitable examples include, without limitation, nitrogen, argon, xenon, helium or mixtures thereof. Preferably, the inert atmosphere is argon or nitrogen, more preferably argon. The inert atmosphere may flow over the surface of the catalyst precursor or may not flow thereover (a static environment). When the inert atmosphere does flow over the surface of the catalyst precursor, the flow rate can vary over a wide range, e.g., at a space velocity of from 1 to 500 $hr^{-1}$.

The calcination is usually performed at a temperature of from 350° C. to 850° C., preferably from 400° C. to 700° C., more preferably from 500° C. to 640° C. The calcination is performed for an amount of time suitable to form the aforementioned catalyst. Typically, the calcination is performed for from 0.5 to 30 hours, preferably from 1 to 25 hours, more preferably for from 1 to 15 hours, to obtain the desired promoted mixed metal oxide.

In a preferred mode of operation, the catalyst precursor is calcined in two stages. In the first stage, the catalyst precursor is calcined in an oxidizing environment (e.g. air) at a temperature of from 275° C. to 400° C., preferably from 275° C. to 325° C. for from 15 minutes to 8 hours, preferably for from 1 to 3 hours. In the second stage, the material from the first stage is calcined in a non-oxidizing environment (e.g., an inert atmosphere) at a temperature of from 500° C. to 700° C., preferably for from 550° C. to 650° C., for 15 minutes to 8 hours, preferably for from 1 to 3 hours. Optionally, a reducing gas, such as, for example, ammonia or hydrogen, may be added during the second stage calcination.

In a particularly preferred mode of operation, the catalyst precursor in the first stage is placed in the desired oxidizing atmosphere at room temperature and then raised to the first stage calcination temperature and held there for the desired first stage calcination time. The atmosphere is then replaced with the desired non-oxidizing atmosphere for the second stage calcination, the temperature is raised to the desired second stage calcination temperature and held there for the desired second stage calcination time.

Although any type of heating mechanism, e.g., a furnace, may be utilized during the calcination, it is preferred to conduct the calcination under a flow of the designated gaseous environment. Therefore, it is advantageous to conduct the calcination in a bed with continuous flow of the desired gas(es) through the bed of solid catalyst precursor particles.

With calcination, a catalyst is formed having the formula $A_aD_bE_cX_dO_e f$ wherein A, D, E, X, O, a, b, c, d and e are as previously defined.

The starting materials for the above promoted mixed metal oxide are not limited to those described above. A wide range of materials including, for example, oxides, nitrates, halides or oxyhalides, alkoxides, acetylacetonates, and organometallic compounds may be used. For example, ammonium heptamolybdate may be utilized for the source of molybdenum in the catalyst. However, compounds such as $MoO_3$, $MoO_2$, $MoCl_5$, $MoOCl_4$, $Mo(OC_2H_5)_5$, molybdenum acetylacetonate, phosphomolybdic acid and silicomolybdic acid may also be utilized instead of ammonium heptamolybdate. Similarly, ammonium metavanadate may be utilized for the source of vanadium in the catalyst. However, compounds such as $V_2O_5$, $V_2O_3$, $VOCl_3$, $VCl_4$, $VO(OC_2H_5)_3$, vanadium acetylacetonate and vanadyl acetylacetonate may also be utilized instead of ammonium metavanadate. The tellurium source may include telluric acid, $TeCl_4$, $Te(OC_2H_5)_5$, $Te(OCH(CH_3)_2)_4$ and $TeO_2$. The niobium source may include ammonium niobium oxalate, $Nb_2O_5$, $NbCl_5$, niobic acid or $Nb(OC_2H_5)_5$ as well as the more conventional niobium oxalate.

The catalyst composition, during or after calcination, is treated with the treatment agent, by contacting the catalyst precursors and/or the catalyst, respectively, with a treatment agent selected from the group consisting of hydrogen, alcohols, a source of $NO_x$ (preferably a gaseous source) and mixtures thereof. It will be appreciated that additionally, or alternatively, the treatment agent may be added to the reaction feed composition. Treatment may take place below, at or above room temperature. In elevated temperature treatments, for instance, the treatment agent may be contacted with the catalyst at one or more temperatures greater than 50° C., greater than 100° C., or even greater than 200° C., such as during a calcination step. The amount of time the catalyst is contacted with the treatment agent may vary from as low as a few seconds, to 4 or more hours. The catalyst may be contacted for treating all or a portion of it. In instances where the treatment agent is flowed over or relative to a catalyst, the flow rate may vary as desired, such as on the order of 1 cc/mm, 10 cc/mm, 100 cc/mm or even higher.

A treated mixed metal oxide, thus obtained, exhibits excellent catalytic activities by itself. However, the mixed metal oxide can be converted to a catalyst having higher activities by grinding.

There is no particular restriction as to the grinding method, and conventional methods may be employed. As a dry grinding method, a method of using a gas stream grinder may, for example, be mentioned wherein coarse particles are permitted to collide with one another in a high speed gas stream for grinding. The grinding may be conducted not only mechanically but also by using a mortar or the like in the case of a small scale operation.

As a wet grinding method wherein grinding is conducted in a wet state by adding water or an organic solvent to the above mixed metal oxide, a conventional method of using a rotary cylinder-type medium mill or a medium-stirring type mill, may be mentioned. The rotary cylinder-type medium mill is a wet mill of the type wherein a container for the object to be ground is rotated, and it includes, for example, a ball mill and a rod mill. The medium-stirring type mill is a wet mill of the type wherein the object to be ground, contained in a container is stirred by a stirring apparatus, and it includes, for example, a rotary screw type mill, and a rotary disc type mill.

The conditions for grinding may suitably be set to meet the nature of the above-mentioned promoted mixed metal oxide, the viscosity, the concentration, etc. of the solvent used in the case of wet grinding, or the optimum conditions of the grinding apparatus. However, it is preferred that grinding is conducted until the average particle size of the ground catalyst precursor would usually be at most 20 $\mu m$, more preferably at most 5 $\mu m$. Improvement in the catalytic performance may occur due to such grinding.

Further, in some cases, it is possible to further improve the catalytic activities by further adding a solvent to the ground catalyst precursor to form a solution or slurry, followed by drying again. There is no particular restriction as to the concentration of the solution or slurry, and it is usual to adjust the solution or slurry so that the total amount of the starting material compounds for the ground catalyst precursor is from 10 to 60 wt %. Then, this solution or slurry is dried by a method such as spray drying, freeze drying, evaporation to dryness or vacuum drying, preferably by the spray drying method. Further, similar drying may be conducted also in the case where wet grinding is conducted.

The oxide obtained by the above-mentioned method may be used as a final catalyst, but it may further be subjected to heat treatment usually at a temperature of from 200° to 700° C. for from 0.1 to 10 hours.

The present invention also provides a process for producing an unsaturated carboxylic acid, which comprises subjecting an alkane, or a mixture of an alkane and an alkene, to a vapor phase catalytic oxidation reaction in the presence of a catalyst containing the above treated mixed metal oxide, to produce an unsaturated carboxylic acid.

In the production of such an unsaturated carboxylic acid, it is preferred to employ a starting material gas that contains steam. In such a case, as a starting material gas to be supplied to the reaction system, a gas mixture comprising a steam-containing alkane, or a steam-containing mixture of alkane and alkene, and an oxygen-containing gas, is usually used. However, the steam-containing alkane, or the steam-containing mixture of alkane and alkene, and the oxygen-containing gas may be alternately supplied to the reaction system. The steam to be employed may be present in the form of steam gas in the reaction system, and the manner of its introduction is not particularly limited.

Further, as a diluting gas, an inert gas such as nitrogen, argon or helium may be supplied. The molar ratio (alkane or mixture of alkane and alkene):(oxygen):(diluting gas):($H_2O$) in the starting material gas is preferably (1):(0.1 to 10):(0 to 20):(0.2 to 70), more preferably (1):(1 to 5.0):(0 to 10):(5 to 40).

When steam is supplied together with the alkane, or the mixture of alkane and alkene, as starting material gas, the selectivity for an unsaturated carboxylic acid is distinctly improved, and the unsaturated carboxylic acid can be obtained from the alkane, or mixture of alkane and alkene, in good yield simply by contacting in one stage. However, the conventional technique utilizes a diluting gas such as nitrogen, argon or helium for the purpose of diluting the starting material. As such a diluting gas, to adjust the space velocity, the oxygen partial pressure and the steam partial pressure, an inert gas such as nitrogen, argon or helium may be used together with the steam.

As the starting material alkane it is preferred to employ a $C_{3-8}$ alkane, particularly propane, isobutane or n-butane; more preferably, propane or isobutane; most preferably, propane. According to the present invention, from such an alkane, an unsaturated carboxylic acid such as an α,β-unsaturated carboxylic acid can be obtained in good yield. For example, when propane or isobutane is used as the starting material alkane, acrylic acid or methacrylic acid will be obtained, respectively, in good yield.

In the present invention, as the starting material mixture of alkane and alkene, it is preferred to employ a mixture of $C_{3-8}$ alkane and $C_{3-8}$ alkene, particularly propane and propene, isobutane and isobutene or n-butane and n-butene. As the starting material mixture of alkane and alkene, propane and propene or isobutane and isobutene are more preferred. Most preferred is a mixture of propane and propene. According to the present invention, from such a mixture of an alkane and an alkene, an unsaturated carboxylic acid such as an α,β-unsaturated carboxylic acid can be obtained in good yield. For example, when propane and propene or isobutane and isobutene are used as the starting material mixture of alkane and alkene, acrylic acid or methacrylic acid will be obtained, respectively, in good yield. Preferably, in the mixture of alkane and alkene, the alkene is present in an amount of at least 0.5% by weight, more preferably at least 1.0% by weight to 95% by weight; most preferably, 3% by weight to 90% by weight.

As an alternative, an alkanol, such as isobutanol, which will dehydrate under the reaction conditions to form its corresponding alkene, i.e. isobutene, may also be used as a feed to the present process or in conjunction with the previously mentioned feed streams.

The purity of the starting material alkane is not particularly limited, and an alkane containing a lower, alkane such as methane or ethane, air or carbon dioxide, as impurities, may be used without any particular problem. Further, the starting material alkane may be a mixture of various alkanes. Similarly, the purity of the starting material mixture of alkane and alkene is not particularly limited, and a mixture of alkane and alkene containing a lower alkene such as ethene, a lower alkane such as methane or ethane, air or carbon dioxide, as impurities, may be used without any particular problem. Further, the starting material mixture of alkane and alkene may be a mixture of various alkanes and alkenes.

There is no limitation on the source of the alkene. It may be purchased, per se, or in admixture with an alkane and/or other impurities. Alternatively, it can be obtained as a by-product of alkane oxidation. Similarly, there is no limitation on the source of the alkane. It may be purchased, per se, or in admixture with an alkene and/or other impurities. Moreover, the alkane, regardless of source, and the alkene, regardless of source, may be blended as desired.

The detailed mechanism of the oxidation reaction of the present invention is not clearly understood, but the oxidation reaction is carried out by oxygen atoms present in the above mixed metal oxide or by molecular oxygen present in the feed gas. To incorporate molecular oxygen into the feed gas, such molecular oxygen may be pure oxygen gas. However, it is usually more economical to use an oxygen-containing gas such as air, since purity is not particularly required.

It is also possible to use only an alkane, or a mixture of alkane and alkene, substantially in the absence of molecular oxygen for the vapor phase catalytic reaction. In such a case, it is preferred to adopt a method wherein a part of the catalyst is appropriately withdrawn from the reaction zone from time to time, then sent to an oxidation regenerator, regenerated and then returned to the reaction zone for reuse. As the regeneration method of the catalyst, a method may, for example, be mentioned which comprises contacting an oxidative gas such as oxygen, air or nitrogen monoxide with the catalyst in the regenerator usually at a temperature of from 300° to 600° C.

A process for producing an unsaturated carboxylic acid may also be employed where propane is used as the starting material alkane, and air is used as the oxygen source. In such an instance, the reaction system may be preferably a fixed bed system. The proportion of air to be supplied to the reaction system is important for the selectivity for the resulting acrylic acid, and it is usually at most 25 moles, preferably from 0.2 to 18 moles per mole of propane, whereby high selectivity for acrylic acid can be obtained. This reaction can be conducted usually under atmospheric pressure, but may be conducted under a slightly elevated pressure or slightly reduced pressure. With respect to other alkanes such as isobutane, or to mixtures of alkanes and alkenes such as propane and propene, the composition of the feed gas may be selected in accordance with the conditions for propane.

Typical reaction conditions for the oxidation of propane or isobutane to acrylic acid or methacrylic acid may be utilized in the practice of the present invention. The process may be practiced in a single pass mode (only fresh feed is fed to the reactor) or in a recycle mode (at least a portion of the reactor effluent is returned to the reactor). General conditions for the process of the present invention are as follows: the reaction temperature can vary from 200° C. to 700° C., but is usually in the range of from 200° C. to 550° C., more preferably 250° C. to 480° C., most preferably 300° C. to 400° C.; the gas space velocity, SV, in the vapor phase reaction is usually within a range of from 100 to 10,000 $hr^{-1}$, preferably 300 to 6,000 $hr^{-1}$, more preferably 300 to 2,000 $hr^{-1}$; the average contact time with the catalyst can be from 0.01 to 10 seconds or more, but is usually in the range of from 0.1 to 10 seconds, preferably from 0.2 to 6 seconds; the pressure in the reaction zone usually ranges from 0 to 75 psig, but is preferably no more than 50 psig. In a single pass mode process, it is preferred that the oxygen be supplied from an oxygen-containing gas such as air. The single pass mode process may also be practiced with oxygen addition. In the practice of the recycle mode process, oxygen gas by itself is the preferred source so as to avoid the build up of inert gases in the reaction zone.

Of course, in the oxidation reaction of the present invention, it is important that the hydrocarbon and oxygen concentrations in the feed gases be maintained at the appropriate levels to minimize or avoid entering a flammable regime within the reaction zone or especially at the outlet of the reactor zone. Generally, it is preferred that the outlet oxygen levels be low to both minimize after-burning and, particularly, in the recycle mode of operation, to minimize the amount of oxygen in the recycled gaseous effluent stream. In addition, operation of the reaction at a low temperature (below 450° C.) is extremely attractive because after-burning becomes less of a problem, which enables the attainment of higher selectivity to the desired products. The catalyst of the present invention operates more efficiently at the lower temperature range set forth above, significantly reducing the formation of acetic acid and carbon oxides, and increasing selectivity to acrylic acid. As a diluting gas to adjust the space velocity and the oxygen partial pressure, an inert gas such as nitrogen, argon or helium may be employed.

When the oxidation reaction of propane, and especially the oxidation reaction of propane and propene, is conducted by the method of the present invention, carbon monoxide, carbon dioxide, acetic acid, etc. may be produced as by-products, in addition to acrylic acid. Further, in the method of the present invention, an unsaturated aldehyde may sometimes be formed depending upon the reaction conditions. For example, when propane is present in the starting material mixture, acrolein may be formed; and when isobutane is present in the starting material mixture, methacrolein may be formed. In such a case, such an unsaturated aldehyde can be converted to the desired unsaturated carboxylic acid by subjecting it again to the vapor phase catalytic oxidation with the promoted mixed metal oxide-containing catalyst of the present invention or by subjecting it to a vapor phase catalytic oxidation reaction with a conventional oxidation reaction catalyst for an unsaturated aldehyde.

In yet another aspect, the method of the present invention comprises subjecting an alkane, or a mixture of an alkane and an alkene, to a vapor phase catalytic oxidation reaction with ammonia in the presence of a catalyst containing the above treated mixed metal oxide, to produce an unsaturated nitrile.

In the production of such an unsaturated nitrile, as the starting material alkane, it is preferred to employ a $C_{3-8}$alkane such as propane, butane, isobutane, pentane, hexane and heptane. However, in view of the industrial application of nitrites to be produced, it is preferred to employ a lower alkane having 3 or 4 carbon atoms, particularly propane and isobutane.

Similarly, as the starting material mixture of alkane and alkene, it is preferred to employ a mixture of $C_{3-8}$alkane and $C_{3-8}$alkene such as propane and propene, butane and butene, isobutane and isobutene, pentane and pentene, hexane and hexene, and heptane and heptene. However, in view of the industrial application of nitrites to be produced, it is more preferred to employ a mixture of a lower alkane having 3 or 4 carbon atoms and a lower alkene having 3 or 4 carbon atoms, particularly propane and propene or isobutane and isobutene. Preferably, in the mixture of alkane and alkene, the alkene is present in an amount of at least 0.5% by weight, more preferably at least 1.0% by weight to 95% by weight, most preferably 3% by weight to 90% by weight.

The purity of the starting material alkane is not particularly limited, and an alkane containing a lower alkane such as methane or ethane, air or carbon dioxide, as impurities, may be used without any particular problem. Further, the starting material alkane may be a mixture of various alkanes. Similarly, the purity of the starting material mixture of alkane and alkene is not particularly limited, and a mixture of alkane and alkene containing a lower alkene such as ethene, a lower alkane such as methane or ethane, air or carbon dioxide, as impurities, may be used without any particular problem. Further, the starting material mixture of alkane and alkene may be a mixture of various alkanes and alkenes.

There is no limitation on the source of the alkene. It may be purchased, per se, or in admixture with an alkane and/or other impurities. Alternatively, it can be obtained as a by-product of alkane oxidation. Similarly, there is no limitation on the source of the alkane. It may be purchased, per se, or in admixture with an alkene and/or other impurities. Moreover, the alkane, regardless of source, and the alkene, regardless of source, may be blended as desired.

The detailed mechanism of the ammoxidation reaction of this aspect of the present invention is not clearly understood. However, the oxidation reaction is conducted by the oxygen atoms present in the above promoted mixed metal oxide or by the molecular oxygen in the feed gas. When molecular oxygen is incorporated in the feed gas, the oxygen may be pure oxygen gas. However, since high purity is not required, it is usually economical to use an oxygen-containing gas such as air.

As the feed gas, it is possible to use a gas mixture comprising an alkane, or a mixture of an alkane and an alkene, ammonia and an oxygen-containing gas, However, a gas mixture comprising an alkane or a mixture of an alkane and an alkene and ammonia, and an oxygen-containing gas may be supplied alternately.

When the gas phase catalytic reaction is conducted using an alkane, or a mixture of an alkane and an alkene, and ammonia substantially free from molecular oxygen, as the feed gas, it is advisable to employ a method wherein a part of the catalyst is periodically withdrawn and sent to an oxidation regenerator for regeneration, and the regenerated catalyst is returned to the reaction zone. As a method for regenerating the catalyst, a method may be mentioned wherein an oxidizing gas such as oxygen, air or nitrogen monoxide is permitted to flow through the catalyst in the regenerator usually at a temperature of from 300° C. to 600° C.

A process may also be employed where propane is used as the starting material alkane, and air is used as the oxygen source. The proportion of air to be supplied for the reaction is important with respect to the selectivity for the resulting acrylonitrile. Namely, high selectivity for acrylonitrile is obtained when air is supplied within a range of at most 25 moles, particularly 1 to 15 moles, per mole of the propane. The proportion of ammonia to be supplied for the reaction is preferably within a range of from 0.2 to 5 moles, particularly from 0.5 to 3 moles, per mole of propane. This reaction may usually be conducted under atmospheric pressure, but may be conducted under a slightly increased pressure or a slightly reduced pressure. With respect to other alkanes such as isobutane, or to mixtures of alkanes and alkenes such as propane and propene, the composition of the feed gas may be selected in accordance with the conditions for propane.

The process of the third aspect of the present invention may be conducted at a temperature of, for example, from 250° C. to 480° C. More preferably, the temperature is from 300° C. to 400° C. The gas space velocity, SV, in the gas phase reaction is usually within the range of from 100 to 10,000 $hr^{-1}$, preferably from 300 to 6,000 $hr^{-1}$, more preferably from 300 to 2,000 $hr^{-1}$. As a diluent gas, for adjusting the space velocity and the oxygen partial pressure, an inert gas such as nitrogen, argon or helium can be employed. When ammoxidation of propane is conducted by the method of the present invention, in addition to acrylonitrile, carbon monoxide, carbon dioxide, acetonitrile, hydrocyanic acid and acrolein may form as by-products.

The examples set forth below are for illustrative purposes only and should not be considered as limiting the scope of the invention.

EXAMPLES

Example 1–5

In a flask containing 390 g of water, 46.4 g of ammonium heptamolybdate tetrahydrate (Aldrich Chemical Company), 9.2 g of ammonium metavanadate (Alfa-Aesar) and 13.9 g of telluric acid (Aldrich Chemical Company) were dissolved upon heating to 80° C. After cooling to 20° C., 201.3 g of an aqueous solution of niobium oxalate (Reference Metals Company) containing 10.44 mmole/g of niobium was mixed to obtain a solution. The water of this solution was removed via a rotary evaporator with a warm water bath at 50° C. and 28 mm/Hg to obtain 73 g of precursor solid. 25 g of the catalyst precursor solid was calcined in a quartz tube by flowing argon, at 600° C. for 2 hours. The oven had previously been heated to 275° C. and held for one hour, then ramped to 600° C. The flow rate of Ar was set at 100 cc/min. The catalyst thus obtained was pressed in a mold and then broken and sieved to 10–20 mesh granules. Approximately 0.5 g of the granules were packed into a quartz tube reactor for gas phase propane oxidation. The oxidation was conducted with a feed ratio of propane/steam/air/ of 1/3/96. The effluent from the reactor was analyzed by infrared spectrometry (IR) to determine the propane conversion and for the yield of acrylic acid. The results are shown in Table 1, with varying oxidation reaction temperatures as between the different samples.

TABLE 1

| Example # | Residence Time (sec) | Temperature (° C.) | % $C_3$ Conversion | % AA Selectivity | % AA Yield |
|---|---|---|---|---|---|
| 1 | 3 | 280 | 12.1 | 44.8 | 5.4 |
| 2 | 3 | 330 | 33.2 | 41.6 | 13.8 |
| 3 | 3 | 350 | 46.0 | 32.6 | 15.0 |
| 4 | 3 | 370 | 59.3 | 20.9 | 12.4 |
| 5 | 3 | 380 | 65.9 | 16.2 | 10.7 |

Examples 6–10

The catalyst prepared in example 1 was calcined in 4% hydrogen (96% $N_2$) at 280° C. Approximately 0.5 g of the granules were packed into a quartz tube reactor for gas phase propane oxidation. The oxidation was conducted with a feed ratio of propane/steam/air/ of 1/3/96. The effluent from the reactor was analyzed by infrared spectrometry (IR) to determine the propane conversion and for the yield of acrylic acid. The results at the respective different oxidation reaction temperatures are shown in Table 2.

TABLE 2

| Example # | Residence Time (sec) | Temperature (° C.) | % $C_3$ Conversion | % AA Selectivity | % AA Yield |
|---|---|---|---|---|---|
| 6 | 3 | 280 | 10.8 | 61.9 | 6.7 |
| 7 | 3 | 330 | 30.8 | 54.7 | 16.9 |
| 8 | 3 | 350 | 43.5 | 38.8 | 16.9 |
| 9 | 3 | 370 | 55.9 | 23.0 | 12.9 |
| 10 | 3 | 380 | 62.1 | 17.2 | 10.7 |

Examples 11–15

The catalyst prepared in example 1 was calcined in 4% hydrogen (96% $N_2$) at 325° C. Approximately 0.5 g of the granules were packed into a quartz tube reactor for gas phase propane oxidation. The oxidation was conducted with a feed ratio of propane/steam/air/ of 1/3/96. The effluent from the reactor was analyzed by infrared spectrometry (IR) to determine the propane conversion and for the yield of acrylic acid. The results at the respective different oxidation reaction temperatures are shown in Table 3.

TABLE 3

| Example # | Residence Time (sec) | Temperature (° C.) | % $C_3$ Conversion | % AA Selectivity | % AA Yield |
|---|---|---|---|---|---|
| 11 | 3 | 280 | 11.9 | 84.3 | 10.0 |
| 12 | 3 | 330 | 31.1 | 72.5 | 22.6 |
| 13 | 3 | 350 | 42.8 | 49.0 | 21.0 |
| 14 | 3 | 370 | 55.9 | 24.5 | 13.7 |
| 15 | 3 | 380 | 61.6 | 15.9 | 9.8 |

Examples 16–20

The catalyst prepared in example 1 was calcined in 4% hydrogen (96% $N_2$) at 400° C. Approximately 0.5 g of the granules were packed into a quartz tube reactor for gas phase propane oxidation. The oxidation was conducted with a feed ratio of propane/steam/air/ of 1/3/96. The effluent from the reactor was analyzed by infrared spectrometry (IR) to determine the propane conversion and for the yield of acrylic acid. The results at the respective different oxidation reaction temperatures are shown in Table 4.

TABLE 4

| Example # | Residence Time (sec) | Temperature (° C.) | % $C_3$ Conversion | % AA Selectivity | % AA Yield |
|---|---|---|---|---|---|
| 16 | 3 | 280 | 10.0 | 74.0 | 7.4 |
| 17 | 3 | 330 | 28.6 | 62.6 | 17.9 |
| 18 | 3 | 350 | 39.5 | 56.4 | 22.3 |
| 19 | 3 | 370 | 53.5 | 34.4 | 18.4 |
| 20 | 3 | 380 | 58.8 | 24.0 | 14.1 |

Example 21–25

A catalyst was prepared using stock metal solutions where solution 1 contained Mo, V and Te in the correct ratios and solution 2 contained Nb and oxalic acid in the right proportions. The catalyst was made by mixing solution 1 and solution 2. The water of this solution was removed via a rotary evaporator with a m water bath at 50° C. and 28 mm/Hg to obtain the precursor solid. This catalyst precursor solid was calcined in a quartz tube by flowing argon, at 600° C. for 2 hours. The oven had previously been heated to 275° C. and held for one hour, then ramped to 600° C. The flow rate of Ar was set at 100 cc/min. The catalyst thus obtained was pressed in a mold and then broken and sieved to 10–20 mesh granules. Approximately 0.5 g of the granules were packed into a quartz tube reactor for gas phase propane oxidation. The oxidation was conducted with a feed ratio of propane/steam/air/ of 1/3/96. The effluent from the reactor was analyzed by infrared spectrometry (IR) to determine the propane conversion and for the yield of acrylic acid. The results at the respective different oxidation reaction temperatures are shown in Table 5.

TABLE 5

| Example # | Residence Time (sec) | Temperature (° C.) | % $C_3$ Conversion | % AA Selectivity | % AA Yield |
|---|---|---|---|---|---|
| 21 | 3 | 360 | 8.0 | 50.0 | 4.0 |
| 22 | 3 | 370 | 11.0 | 45.0 | 5.0 |
| 23 | 3 | 380 | 13.0 | 54.0 | 7.0 |
| 24 | 3 | 390 | 16.0 | 50.0 | 8.0 |
| 25 | 3 | 400 | 19.0 | 42.0 | 8.0 |

Example 26–31

Approximately 10 g of the multi metal oxide catalyst used in example 21 was refluxed in 100 cc methanol for 1.5 hour. The methanol was subsequently removed via a rotary evaporator with a warm water bath at 50° C. and 28 mm/Hg to obtain the solid catalyst. This was then dried in a vacuum oven for 72 hours. The catalyst thus obtained was pressed in a mold and then broken and sieved to 10–20 mesh granules. Approximately 0.5 g of the granules were packed into a quartz tube reactor for gas phase propane oxidation. The oxidation was conducted with a feed ratio of propane/steam/air/ of 1/3/96. The effluent from the reactor was analyzed by infrared spectrometry (IR) to determine the propane conversion and for the yield of acrylic acid. The results at the respective different oxidation reaction temperatures are shown in Table 6.

TABLE 6

| Example # | Residence Time (sec) | Temperature (° C.) | % C$_3$ Conversion | % AA Selectivity | % AA Yield |
|---|---|---|---|---|---|
| 26 | 3 | 350 | 9.0 | 56.0 | 5.0 |
| 27 | 3 | 360 | 11.0 | 64.0 | 7.0 |
| 28 | 3 | 370 | 15.0 | 60.0 | 9.0 |
| 29 | 3 | 380 | 19.0 | 58.0 | 11.0 |
| 30 | 3 | 390 | 22.0 | 50.0 | 11.0 |
| 31 | 3 | 400 | 26.0 | 44.0 | 12.0 |

Examples 32–34

A catalyst was prepared using stock metal solutions where solution 1 contained Mo, V and Te in the correct ratios and solution 2 contained Nb and oxalic acid in the right proportions. The catalyst was made by mixing solution 1 and solution 2. The water of this solution was removed via a rotary evaporator with a warm water bath at 50° C. and 28 mm/Hg to obtain the precursor solid. This catalyst precursor solid was calcined in a quartz tube by flowing argon, at 600° C. for 2 hours. The oven had previously been heated to 275° C. and held for one hour, then ramped to 600° C. The flow rate of Ar was set at 100 cc/min. The catalyst thus obtained was pressed in a mold and then broken and sieved to 10–20 mesh granules. Approx. 0.6 g of the granules were packed into a quartz tube reactor for gas phase propane oxidation. The oxidation was conducted with a feed ratio of propane/steam/air/of 1/3/96. The effluent from the reactor was analyzed by infra red spectrometry (IR) to determine the propane conversion and for the yield of acrylic acid. The results at the respective different oxidation reaction temperatures are shown in Table 7.

TABLE 7

| Example # | Residence Time (sec) | Temperature (° C.) | % C$_3$ Conversion | % AA Selectivity | % AA Yield |
|---|---|---|---|---|---|
| 32 | 3 | 340 | 47.6 | 52.5 | 25.0 |
| 33 | 3 | 350 | 53.6 | 40.7 | 21.8 |
| 34 | 3 | 370 | 64.6 | 18.6 | 12.0 |

Example 35–37

A fresh charge of approximately 0.6 g of the catalyst granules used in example 32 was packed into a quartz tube reactor and treated at 800° C. with a nitrogen gas stream (12.5 cc/min flow rate) containing 14% methanol for 30 min. Nitrogen with no added methanol (12.5/min flow rate) was then passed over the catalyst bed at 400° C. for 30 min. before lowering the catalyst bed to 330° C. while continuing to flow nitrogen (12.5/min flow rate). The oxidation was conducted with a feed ratio of propane/steam/air of 1/3/96. The effluent from the reactor was analyzed by infrared spectrometry (IR) to determine the propane conversion and for the yield of acrylic acid. The results are shown in Table 8. XRD analysis, before and after methanol treatment, of the catalyst indicated no phase changes had occurred.

TABLE 8

| Example # | Residence Time (sec) | Temperature (° C.) | % C$_3$ Conversion | % AA Selectivity | % AA Yield |
|---|---|---|---|---|---|
| 35 | 3 | 340 | 44.3 | 64.5 | 28.6 |
| 36 | 3 | 350 | 49.1 | 52.3 | 25.7 |
| 37 | 3 | 370 | 63.2 | 26.0 | 16.5 |

Examples 38–39

Example 38

Approximately 100 mL of an aqueous solution containing ammonium heptamolybdate tetrahydrate (1.0M Mo), ammonium metavanadate (0.3M V) and telluric acid (0.23 Te), formed by dissolving the corresponding salts in water at 70° C., was added to a 1000 mL rotavap flask. Then 50 mL of an aqueous solution of niobium oxalate (0.16M Nb) and oxalic acid (0.58M) were added thereto. After removing the water via a rotary evaporator with a warm water bath at 50° C. and 28 mm/Hg, the solid materials were further dried in a vacuum oven at 25° C. overnight and then calcined. Calcination was effected by placing the solid materials in an air atmosphere and then heating them to 275° C. at 10° C./min and holding them under the air atmosphere at 275° C. for one hour; the atmosphere was then changed to argon and the material was heated from 275° C. to 600° C. at 2° C./min and the material was held under the argon atmosphere at 600° C. for two hours. The final catalyst had a nominal composition of $Mo_1V_{0.3}Te_{0.23}Nb_{0.08}O_f$. The catalyst, thus obtained, was pressed in a mold and then broken and sieved to 10–20 mesh granules for evaluation.

Example 39

Approximately 6 grams of catalysts from example 1 were ground and placed in a quartz tube and were held in position with quartz wool at approximately mid-length in the tube. Argon gas (100 mL/min) flows first through a saturator containing 30% aqueous $HNO_3$ at 40° C. and then through the catalyst in the quartz tube. The catalysts were held at 25° C. for 4 hours to saturate with $HNO_3$, then heated to 600° C. at 10° C./min and held at 600° C. for 2 hours. The catalyst, thus treated, was pressed in a mold and then broken and sieved to 10–20 mesh granules for reactor evaluation.

Catalysts were evaluated in a 10 cm long Pyrex tube reactor (internal diameter: 3.9 mm). The catalyst bed (4 cm long) was positioned with glass wool at approximately mid-length in the reactor and was heated with an electric furnace. Mass flow controllers and meters regulated the gas flow rate. The oxidation was conducted using a feed gas stream of propane, steam and air, with a feed ratio of propane:steam:air of 1:3:96. The reactor effluent was analyzed by an FTIR.

The results at 390° C. and at a 3 second residence time are shown in Table 9.

TABLE 9

| Example | Temp. C. | Residence Time (sec) | % C$_3$ Conversion | % AA yield |
|---|---|---|---|---|
| 38 | 390 | 3 | 41 | 17 |
| 39 | 390 | 3 | 51 | 26 |

What is claimed is:

1. A process for improving the performance characteristics of a catalyst, comprising the steps of:
   a) providing precursors for a mixed metal oxide having the empirical formula $A_aD_bE_cX_dO_e$, wherein A is at least one element selected from the group consisting of Mo and W, D is at least one element selected from the group consisting of V and Ce, E is at least one element selected from the group consisting of Te, Sb and Se, and X is at least one element selected from the group consisting of Nb, Ta, Ti, Al, Zr, Cr, Mn, Fe, Ru, Co, Rh, Ni, Pt, Sb, Bi, B, In, As, Ge, Sn, Li, Na, K, Rb, Cs, Fr, Be, Mg, Ca, Sr, Ba, Ra, Hf, Ag, Pb, P, Pm, Eu, Gd, Dy, Ho, Er, Tm, Yb and Lu; and a=1, b=0.01 to 1.0, c= 0.01 to 1.0, d=0.01 to 1.0, and e is dependent on the oxidation state of said other elements;
   b) calcining an admixture of said precursors; and
   c) contacting, no earlier than during said calcining step (b), said precursors with a treatment agent selected from the group consisting of hydrogen, a gaseous source of $NO_x$ and mixtures thereof.

2. The process according to claim 1, wherein said treatment agent is hydrogen.

3. The process according to claim 1, wherein said treatment agent is a gaseous source of $NO_x$ selected from the group consisting of NO, $N_2O$, $NO_2$ and mixtures thereof.

4. A catalytic process, comprising the steps of:
   a) providing precursors for a mixed metal oxide having the empirical formula $A_aD_bE_cX_dO_e$, wherein A is at least one element selected from the group consisting of Mo and W, D is at least one element selected from the group consisting of V and Ce, E is at least one element selected from the group consisting of Te, Sb and Se, and X is at least one element selected from the group consisting of Nb, Ta, Ti, Al, Zr, Cr, Mn, Fe, Ru, Co, Rh, Ni, Pt, Sb, Bi, B, In, As, Ge, Sn, Li, Na, K, Rb, Cs, Fr, Be, Mg, Ca, Sr, Ba, Ra, Hf, Ag, Pb, P, Pm, Eu, Gd, Dy, Ho, Er, Tm, Yb and Lu; and a=1, b=0.01 to 1.0, c= 0.01 to 1.0, d=0.01 to 1.0, and e is dependent on the oxidation state of said other elements;
   b) calcining an admixture of said precursors;
   c) contacting, no earlier than said calcining step (b), said precursors with a treatment agent selected from the group consisting of hydrogen, gaseous NO, gaseous $N_2O$, gaseous $NO_2$ and mixtures thereof; and
   d) subjecting a feed including an alkane or a mixture of an alkane and an alkene to a vapor phase catalytic oxidation reaction in the presence of said catalyst.

5. The process according to claim 4, wherein said feed of said subjecting step (d) further includes ammonia.

* * * * *